United States Patent
Nikoloudis et al.

(10) Patent No.: US 11,571,662 B2
(45) Date of Patent: Feb. 7, 2023

(54) FILTER MODULE HAVING AN EDGE-REINFORCED MEMBRANE, METHOD FOR PRODUCING THE FILTER MODULE AND USE THEREOF

(71) Applicant: Sartorius Stedim Biotech GmbH, Goettingen (DE)

(72) Inventors: Paschalis Nikoloudis, Goettingen (DE); Sebastian Handt, Goettingen (DE); Thomas Loewe, Goettingen (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 155 days.

(21) Appl. No.: 17/023,691

(22) Filed: Sep. 17, 2020

(65) Prior Publication Data
US 2021/0001277 A1   Jan. 7, 2021

Related U.S. Application Data

(63) Continuation of application No. PCT/EP2019/056696, filed on Mar. 18, 2019.

(30) Foreign Application Priority Data

Mar. 19, 2018   (DE) ..................... 10 2018 002 261.8

(51) Int. Cl.
*B01D 53/22*   (2006.01)
*B01D 65/00*   (2006.01)
(Continued)

(52) U.S. Cl.
CPC ......... *B01D 65/003* (2013.01); *B01D 46/543* (2013.01); *B01D 63/067* (2013.01);
(Continued)

(58) Field of Classification Search
CPC .. B01D 71/36; B01D 2313/21; B01D 63/067; B01D 65/003; B01D 46/543; B01D 2279/65; B01D 2313/04; B01D 71/68
See application file for complete search history.

(56) References Cited

U.S. PATENT DOCUMENTS 4,392,958 A * 7/1983 Ganzi ................. B01D 63/061
                                                    264/DIG. 48
4,419,241 A * 12/1983 Hoffmann ............ B01D 29/111
                                                    55/497
(Continued)

FOREIGN PATENT DOCUMENTS

DE   9305041 U1   6/1993
DE   19543955 A1  5/1997
(Continued)

OTHER PUBLICATIONS

Rene Israel Peinador Davila, "Characterization for Ultra and Nanofiltration Commerical Filters By Liquid-Liquid Displaement Porosimetry", University of Valladolid, (2015), 133 pages.
(Continued)

*Primary Examiner* — Anthony R Shumate
(74) *Attorney, Agent, or Firm* — Edell, Shapiro & Finnan, LLC (57) ABSTRACT

A filter module for sterile filtration and virus filtration of fluid media. The filter module includes a filter membrane with a porous edge structure arranged thereon and at least one anchoring element. The filter membrane with the porous edge structure is embedded in the anchoring element and serves as edge reinforcement to improve the connection of the filter membrane to the anchoring element. The texturing or surface roughness of the edge reinforcement provides an interlocking effect between the filter membrane and the anchoring element. The embedding of the filter membrane in the anchoring element provides a fluid-tight connection of (Continued)

the membrane to the anchoring element which prevents the occurrence of leaks in the end region of the filter module. A method for producing the filter module is also described.

21 Claims, 3 Drawing Sheets

(51) Int. Cl.
  *B01D 46/54*   (2006.01)
  *B01D 63/06*   (2006.01)
  *B01D 71/36*   (2006.01)
  *B01D 71/68*   (2006.01)

(52) U.S. Cl.
  CPC .............. *B01D 71/36* (2013.01); *B01D 71/68* (2013.01); *B01D 2279/65* (2013.01); *B01D 2313/04* (2013.01); *B01D 2313/21* (2013.01)

(56) References Cited

U.S. PATENT DOCUMENTS

| | | | | |
|---|---|---|---|---|
| 4,512,892 | A * | 4/1985 | Ganzi | B01D 29/111 |
| | | | | 264/DIG. 48 |
| 5,059,374 | A * | 10/1991 | Krueger | B01D 53/22 |
| | | | | 264/254 |
| 5,269,917 | A † | 12/1993 | Stankowski | |
| 5,395,429 | A † | 3/1995 | Sutsko | |
| 5,911,886 | A * | 6/1999 | Delmas | B01D 35/30 |
| | | | | 210/450 |
| 6,186,341 | B1 † | 2/2001 | Konstantin | |
| 6,293,411 | B1 * | 9/2001 | Beer | B01D 69/10 |
| | | | | 210/488 |
| 6,511,600 | B1 | 1/2003 | Ohtani | |
| 6,913,786 | B2 † | 7/2005 | Proulx | |
| 7,828,973 | B2 † | 11/2010 | Connors | |
| 2003/0209485 | A1 * | 11/2003 | Kools | B01D 67/003 |
| | | | | 210/490 |
| 2006/0015136 | A1 * | 1/2006 | Besselink | A61F 2/01 |
| | | | | 606/200 |
| 2007/0163950 | A1 * | 7/2007 | Wechs | B01D 67/0016 |
| | | | | 210/500.41 |
| 2009/0304963 | A1 * | 12/2009 | Doyen | D04B 1/225 |
| | | | | 428/36.1 |
| 2013/0139685 | A1 | 6/2013 | Wuenn et al. | |
| 2014/0227732 | A1 * | 8/2014 | Saqi | G01N 1/31 |
| | | | | 435/29 |
| 2015/0289856 | A1 * | 10/2015 | Saqi | A61B 10/02 |
| | | | | 422/534 |
| 2015/0360181 | A1 * | 12/2015 | Neitzel | B01D 39/1692 |
| | | | | 210/483 |
| 2020/0346159 | A1 * | 11/2020 | Nikoloudis | B01D 46/522 |

FOREIGN PATENT DOCUMENTS

| | | |
|---|---|---|
| DE | 102010044648 B4 | 1/2017 |
| EP | 0139822 A2 | 5/1985 |
| WO | WO-2021102396 A1 * | 5/2021 ............ F03B 13/142 |

OTHER PUBLICATIONS

"Standard Test Method for Determining Bacterial Retention of Membrane Filters Utilized for Liquid Filtration", ASTM International, (2006), 6 pages.
Guidance for Industry, "Q5A Viral Safety Evaluation of Biotechnology Products Derived From Cell Lines of Human or Animal Origin", DHHS, FDA, Sep. 1998, 33 pages.
International Search Report, PCT/EP2019/056696, dated Jun. 3, 2019, 2 pages.
Shrestha, "Characterization of Porous Membranes Via Porometry", B.S. Mechanical Engineering, Institute of Engineering (Nepal), 2008, 103 pages.

\* cited by examiner
† cited by third party

FILTER MODULE HAVING AN EDGE-REINFORCED MEMBRANE, METHOD FOR PRODUCING THE FILTER MODULE AND USE THEREOF

CROSS REFERENCE TO RELATED APPLICATIONS

This is a Continuation of International Application PCT/EP2019/056696 which has an international filing date of Mar. 18, 2019, the disclosure of which is incorporated herein by reference in its entirety. This Continuation also claims priority under 35 U.S.C. § 119(a)-(d) to, and also incorporates by reference, in its entirety, German Patent Application DE 10 2018 002 261.8 filed on Mar. 19, 2018.

FIELD OF INVENTION

A filter module having an edge-reinforced membrane is provided, together with methods for producing and using the filter module.

BACKGROUND

Filter modules for use in sterile-filtration and virus filtration have been described that have anchoring elements in which the two ends of a tubular, optionally pleated, filter membrane are embedded. The embedding is usually achieved by immersion of the edge regions of the membrane into the softened anchoring elements, which are also referred to as end caps. Sealing of the membrane with the end caps in this fashion is intended to ensure the sterility of the filter module.

The above-described filter modules, however, experience problems in that, during the embedding process, the connection of the filter membrane to the anchoring element proves to be inadequate. One reason for this stems from the use of different materials for constructing the membrane and the end caps used for sealing. For example, in the case of air filters, the filter membranes commonly are made of polytetrafluoroethylene, which has super-repellent properties, whereas the end caps commonly are formed from polyolefins such as, for instance, polypropylene. The different surface energies of these materials leads to a poor connection between the materials. Generally, only the end caps, and not the filter membranes, are partially melted during embedding. This results in an adverse effect on the connection of the membrane to the anchoring element.

If the membrane and the anchoring element are not sufficiently connected to one another this can lead to the occurrence of leaks in the filter module, and this, in turn, results in a lack of sterility. However, it is in particular in sterile-filtration and virus filtration that a virtually complete absence of bacteria and viruses is essential.

SUMMARY

Against this background, a filter module is provided in which the membrane and the anchoring element used for sealing are connected so that a sufficient sterility of the filter module is ensured even over a relatively long period of use. Methods for producing such a filter module, and for its use, also are provided.

In a first aspect, a filter module is provided having a membrane with a porous edge structure arranged thereon and further comprising at least one anchoring element, where the membrane having the porous edge structure arranged thereon is embedded in the at least one anchoring element.

The porous edge structure which is arranged on the membrane and which serves as edge reinforcement in the embedding of the membrane in the at least one anchoring element, i.e., is embedded together with the membrane in the anchoring element, improves the connection of the above components in the filter module thus obtained. In particular, this can virtually completely prevent the occurrence of leaks in the region of embedding, especially when the membrane and the porous edge structure arranged thereon are present as a composite. The filter module having an edge-reinforced membrane is fluid-tight in the edge region and thus exhibits excellent sterility even over a relatively long period of use. The filter module suitable for a multiplicity of applications, and is particularly suitable for sterile-filtration and virus filtration of fluid media, particularly of gaseous media, especially of air, as well as of liquid media.

Surprisingly, is was found that the porosity and the texturing or the surface roughness of the edge reinforcement gives rise to an interlocking effect between the filter membrane and the at least one anchoring element, where the edge reinforcement meshes, in a sense, into both the filter membrane and into the at least one anchoring element. The texturing or the surface roughness of the edge reinforcement is first caused by the free spaces spanned by the pores in the porous edge structure, which preferably has a pore size of at least 0.1 µm, and may also be specifically controlled during the production of the filter module as described in more detail further below.

The filter modules described herein are not limited to use of any particular filter membrane, referred to below as "membrane" for the sake of simplicity.

The membrane has a pore size suitable for the intended use, i.e., depending on the size of the particles to be separated. The pore size typically is in the range from 0.005 to 10 µm without being restricted thereto. Advantageously the pore size of the membrane is in a range from 0.01 to 1.2 µm, particular preference being given to a range from 0.02 to 0.45 µm.

To determine pore size, in the context of the invention and in the case of pore sizes of at least 0.1 µm, i.e., for microfiltration membranes having an average pore size of 0.1 to 10 µm, capillary flow porometry is preferably used. This is a gas-liquid porosimetry technique in which the differential gas pressures and flow rates through a membrane sample are measured first in the wet state and then in the dry state. Before the measurement, the membrane sample is contacted with a wetting liquid such that all pores present are filled with said liquid. After the filling of the pores and the introduction of the sample, the measurement cell can be closed and the measurement can be started. After the start of the measurement, the gas pressure is increased in an automatic and stepwise manner and the pore diameters in line with the pressure being applied are emptied as a result of the gas pressure. This is done until the relevant pore range has been captured, i.e., until even the smallest pores present in the measurement range have been cleared of the liquid. Thereafter, the pressure is dropped back down and the measurement is automatically repeated on the now dry sample. From the difference between the two pressure/flow rate curves, the pore size distribution is calculated via the Young-Laplace equation (see also A. Shrestha, "Characterization of porous membranes via porometry", 2012, Mechanical Engineering Graduate Theses & Dissertations, Paper 38, University of Colorado at Boulder).

In the case of pore sizes of at most 0.1 µm, use is preferably made of the liquid-liquid displacement method. It has similarities to capillary flow porometry. However, it is not the gas flow rates that are measured here, but rather the flow rates of the liquid being displaced as a function of the differential pressure increase (see also R. Dávila, "Characterization of ultra and nanofiltration commercial filters by liquid-liquid displacement porosimetry", 2013).

Concerning the thickness of the membrane, the present invention is likewise not subject to further limitation. For example, the membrane thickness can be from 20 to 400 µm, preference being given to a range from 20 to 300 µm.

The geometric shape of the membrane is likewise not subject to any particular limitation so long as the membrane has an edge region which can be provided with the porous edge structure and which is suitable for immersion in the at least one anchoring element. In one embodiment, the membrane has a rectangular shape, with, for example, one of the four edge regions or two opposite edge regions of the membrane being provided with the porous edge structure.

In a particular embodiment, the membrane having the porous edge structure arranged thereon is tubular. To this end, a rectangular membrane can serve as a basis, which is then closed to form a tube, for example by welding. As a result of the tube closure, the ultimately obtained result is a cylindrical arrangement having open end faces. In this connection, the tube closure is effected such that the porous edge structure arranged on the membrane covers one of the two edge regions or both edge regions on the tube exterior along the tube circumference. In an analogous manner, and proceeding from a rectangular membrane, it is also possible to obtain a prism-shaped membrane having, instead of a circular cross-section, a polygonal cross-section, for example a square cross-section. In general, filter modules having a tubular and optionally pleated membrane are referred to as filter cartridges.

Advantageously, the membrane is constructed from a polymer selected from the group consisting of polytetrafluoroethylene (PTFE), polyvinylidene fluoride (PVDF), polyethersulfone (PES), polyamide, polyolefin, cellulose acetate (CA) and cellulose or from mixtures thereof.

Preferably, the membrane of the filter module is constructed from PTFE. Polytetrafluoroethylene has a particularly high chemical resistance over the entire pH scale. Furthermore, PTFE membranes are, as already mentioned above, super-repellent, i.e., they exhibit both hydrophobic and oleophobic properties, and, accordingly, they are suitable for the filtration of virtually all common solvents. Furthermore, polytetrafluoroethylene membranes are distinguished by their thermal resistance, permitting their long-term use even at an elevated temperature, for example at up to 260° C.

If the membrane is constructed from polytetrafluoroethylene, it is furthermore preferred that it is an expanded polytetrafluoroethylene (ePTFE). Expanding the polytetrafluoroethylene during the processing process orientates the individual PTFE strands while reducing the density.

In another preferred embodiment, the membrane is constructed from PES. Polyethersulfones are distinguished by their high resistance to chemicals, by their high thermal stability and by their high impact strength. Optionally, addition of polyvinylpyrrolidone (PVP) or a surface modification can give hydrophilic properties to the PES. The surface of a PES membrane also may be modified in other ways, for example, as described in DE 10 2010 044 648 B4.

A porous edge structure which covers an edge region of the membrane is arranged on the membrane of the filter module. Accordingly, the membrane is thus not completely covered. When mention is made here of the porous edge structure arranged on the membrane, this means that the porous edge structure is arranged on an edge region of the membrane.

As explained above, the arrangement of the porous edge structure on the membrane is not restricted to a single edge region of the membrane. In particular, if the membrane is rectangular and tubular or prism-shaped, as described above, it is possible for the porous edge structure to be arranged on one edge region or on two opposite edge regions of the membrane. So long as the porous edge structure is able to cover an edge region of the membrane, its geometric shape is not subject to any particular limitation. For example, the porous edge structure has a strip form, i.e., it is rectangular, with the strip of the porous edge structure covering an edge region of the membrane. The porous edge structure can, for example, be a porous film or especially a membrane which can, in a specific embodiment, be obtained in strip form, for example by previous cutting of an appropriate planar material.

If the porous edge structure is, for example, present in the form of a strip, the width thereof is typically from 2 to 10 mm, with the region covered by an individual edge strip accounting for about 0.5% to 25% of the total area of the filter membrane without, however, being restricted thereto.

By connection of the membrane and the porous edge structure arranged on it using heat and pressure, occasionally also referred to below as sealing or heat-sealing, it is possible to obtain a firm composite, the required process conditions for the connection operation being selected as a matter of routine by a person skilled in the art. Depending on the context, the porous edge structure arranged on the membrane is to be understood below to mean either the arrangement before the connection or the arrangement after the connection. In a preferred embodiment, the membrane having the porous edge structure arranged thereon is present as a composite, the result being that the filter module is particularly fluid-tight in the edge region at the position of the at least one anchoring element.

The porous edge structure advantageously has a pore size of at least 0.1 µm, particularly preferably of at least 0.2 µm, more preferably of at least 0.4 µm and even more preferably of at least 0.5 µm, for example at least 0.6 µm. The pore size of the porous edge structure is not subject to a particular upper limit, though it is preferably not more than 10 µm. Accordingly, the porous edge structure can have a pore size which exceeds the pore size of the membrane.

If the pores of the porous edge structure are too small, the meshing with the softened end cap will fail to materialize or it is inadequate. This also equally applies to the meshing of the porous edge structure with the membrane. The interlocking effect between the filter membrane and the at least one anchoring element, caused by the edge reinforcement, is, in this case, then merely weak.

The pore size of the porous edge structure may be determined using capillary flow porometry, as described above in connection with the filter membrane.

In general, a particular pore size can, for example, be set during the membrane production process by use of an inert pore former (porogen) of suitable particle size. The pore size can also be set, for example, via mechanical stretching of an appropriate film.

The specific porosities mean that, when immersing the membrane having the porous edge structure arranged thereon into the softened anchoring element, a particularly pronounced connection of the above components can be achieved. Thus, the pores of the porous edge structure are penetrated by the partially melted material of the end cap. For this purpose, it is further preferred that the porous edge structure has a particular texturing or surface roughness, the result being that the connection of the edge-reinforced membrane to the anchoring element is further improved.

It is possible to produce/imprint a texture/surface roughness on the filter membrane while the porous edge structure is being connected to the filter membrane, since a texture is, in a sense, pressed into the filter membrane during the connecting process. For example, this texturing is produced when the filter membrane is transported together with the porous edge structure arranged thereon through a heat sealer via a textured conveyor belt or by guiding a nonwoven along with the porous edge structure and the filter membrane. In both cases, the respective fiber structure of the surrounding medium is stamped into the porous edge structure, with the result being that so-called fiber impressions are produced thereby. The nature of the texturing or of the surface roughness can be determined with the aid of scanning electron microscopy (SEM) and corresponds approximately to the penetration depth of the fiber or to the gap width determined by the fiber diameter, as described further below.

It is preferred that the porous edge structure arranged on the membrane sits flush with the membrane end, i.e., the filter membrane and the edge reinforcement have, in this case, a flush cut. In this case, neither of the above two components projects beyond the other, the result being that a particularly pronounced connection to the end cap occurs during embedding in the anchoring element. In particular, the edge region of the membrane is stabilized during immersion into the softened anchoring element, since the fact that membrane and porous edge structure arranged thereon are sitting flush reduces the risk that the membrane edge region, which has a high degree of elasticity depending on the nature of the material, bends down or bends over.

However, the present invention is not restricted to the porous edge structure arranged on the membrane sitting flush with the membrane end. Thus, the membrane end can also project beyond the edge reinforcement, i.e., the porous edge structure can have a slight distance from the membrane end, for example of up to 1 mm, preferably 0.5 mm and—in accordance with the above embodiments—particularly preferably 0 mm.

The thickness of the porous edge structure is not subject to any particular limitation. It can, for example, be 1/5 to 5/1 of the thickness of the membrane, i.e., the thickness of the porous edge structure can in principle be smaller or larger than the thickness of the membrane. Typical thicknesses of the porous edge structure are in the range from 50 to 400 µm, preferably in the range from 70 to 300 µm, without, however, being restricted thereto.

As already mentioned above, the porous edge structure preferably has a texturing or a surface roughness which can be specifically controlled during production and can be defined via the average penetration depth of the fiber impression and via the average gap width corresponding to the average fiber diameter in a first approximation. The average penetration depth of the fiber impression is preferably from 1 to 200 µm, particularly preferably from 1.5 to 100 µm. The average gap width is preferably from 5 to 900 µm, particularly preferably from 10 to 600 µm. Both penetration depth and gap width can be determined from relevant SEM images of the edge reinforcement using Skandium software (Olympus, version 5.2).

In a preferred embodiment, the porous edge structure arranged on the membrane is constructed from a polymer selected from the group consisting of polyethersulfone, polyamide and polyolefin or from mixtures thereof. The polyolefins can, for example, be polyethylene (PE) or polypropylene (PP) without, however, being restricted thereto. Preferably, the porous edge structure is constructed from polypropylene or polyethersulfone.

In principle, the polymer or polymer mixture from which the porous edge structure is constructed should be able to be softened upon heating. Thus, it has a suitable melting point or melting range which is significantly below the respective decomposition temperature. For example, syndiotactic polypropylene (PP-st) having a degree of crystallization of 30% to 40% has a melting temperature of about 130° C., whereas isotactic polypropylene (PP-it) having a degree of crystallization of 70% to 80% has a melting temperature of about 170° C. Polypropylene decomposes only at temperatures above 330° C.

The description set forth above regarding the melting behavior of the porous edge structure also equally applies to the at least one anchoring element of the filter module.

In a preferred embodiment, the at least one anchoring element is constructed from a polyolefin, such as, for instance, polyethylene or polypropylene, particular preference being given to polypropylene.

Advantageously, the membrane and the porous edge structure have similar material properties, for example with respect to their hydrophilicity or hydrophobicity. This has the advantage that, if there is a protrusion/overhang after embedding in the anchoring element, i.e., if a residual composite composed of membrane and porous edge structure protrudes/overhangs from the end cap, materials of maximum similarity are on top of one another, resulting in an improved filtration performance. For example, it is advantageous for liquid filtration that both the membrane and the porous edge structure are formed from hydrophilic materials. Also, in the case of similar material properties of membrane and porous edge structure, the filter modules are better testable concerning the tightness of the systems.

In a preferred embodiment, the membrane is constructed from (expanded) polytetrafluoroethylene, whereas the porous edge structure arranged on the membrane as well as the at least one anchoring element are both constructed from polypropylene. In a further preferred embodiment that is especially suitable as a liquid filter in virus filtration, both the membrane and the porous edge structure are constructed from polyethersulfone, whereas the at least one anchoring element is constructed from polypropylene.

Concerning the geometric shape of the at least one anchoring element, the filter module is not subject to any particular limitation. A person skilled in the art may select a suitable geometric shape for the at least one anchoring element depending on the intended use, said geometric shape naturally being harmonized with the geometric shape of the membrane having the porous edge structure arranged thereon. In the case of more than one anchoring element, each anchoring element can have an individual geometric shape depending on the intended purpose.

As mentioned above, the membrane having the porous edge structure arranged thereon is embedded in the at least one anchoring element. The membrane edge region on which the porous edge structure is arranged thus immerses into the at least one anchoring element. For this purpose, the at least one anchoring element is softened beforehand by heating. The membrane edge region on which the porous edge structure is arranged need not be completely embedded in the at least one anchoring element. For stability reasons, (a large) part of the porous edge structure can also remain outside the respective anchoring element in the form of a protrusion/overhang. For example, the protrusion/overhang can, measured from the embedding side toward the nonembedded filter membrane, be at least a 1 mm, preferably at least 3 mm and particularly preferably at least 5 mm, and the upper limit of the protrusion/overhang can be 10 mm without, however, being restricted thereto.

The depth of embedding, i.e., the penetration depth of the membrane having the porous edge structure arranged thereon into the at least one anchoring element, is naturally to such an extent that a stable embedding of the membrane is achieved. The depth of embedding is otherwise not subject to any particular limitation. In one embodiment, the immersion depth is 0.5 to 2.5 mm, preferably 0.8 to 2.2 mm and particularly preferably 1.0 to 2.0 mm. An optionally present protrusion or overhang of the porous edge structure, as described above, is not taken into account here.

If the porous edge structure is not arranged just on a single edge region of the membrane, then each membrane edge region on which the porous edge structure is arranged can be embedded in a corresponding anchoring element. For example, the porous edge structure can, as mentioned above, be arranged on two opposite edge regions of a rectangular membrane or a tubular or prism-shaped membrane based thereon, with each edge region having the porous edge structure arranged thereon being embedded in a corresponding anchoring element. In this case, the filter module then comprises two anchoring elements. In particular, it is preferred in the case of a tubular or prism-shaped membrane that the two edge regions of the membrane having the porous edge structure arranged thereon are embedded in corresponding anchoring elements.

According to a further preferred embodiment, the membrane having the porous edge structure arranged thereon is pleated. In this case, both the membrane and the porous edge structure arranged on the membrane assume the fold structure caused by pleating. If the porous edge structure is, for example, present in the form of a strip, pleating is carried out perpendicularly to the longest extent of the strip. If the membrane having the porous edge structure arranged thereon has a tube or prism shape, the folds caused by pleating are oriented in parallel to the main axis of the tube or the prism. A tubular membrane is, by definition, still considered tubular even in the case of a pleating, even if said tubular membrane strictly speaking no longer has a circular cross-section.

If the membrane having the porous edge structure arranged thereon is pleated, the filter surface area can be increased in the filter module while the size of the filter module remains the same. Pleating can also improve the mechanical stability of the filter module. This is especially advantageous when the membrane consists of a comparatively elastic material, this being true for (expanded) polytetrafluoroethylene for example.

According to a further embodiment, the filter module comprises a backflow safeguard and a core in addition to the membrane having the porous edge structure arranged thereon and in addition to the at least one anchoring element. A person skilled in the art will select a suitable backflow safeguard and a suitable core for the filter module depending on the intended use.

Furthermore, the filter module can additionally comprise one or more drainage or support nonwovens. Typically, two nonwovens are provided, wherein these are arranged on both sides of the edge-reinforced filter membrane, i.e., which enclose the membrane having the porous edge structure arranged thereon and thus form the actual separation medium. Like the edge-reinforced filter membrane, an optionally present drainage nonwoven also can be pleated.

Furthermore, the filter module is not restricted to a single filter membrane. For instance, the filter module can comprise, besides the edge-reinforced filter membrane, additionally at least one further filter membrane, which can likewise be edge-reinforced.

A typical sequence of components of a filter module comprises for example—from the outside to the inside—backflow safeguard, drainage nonwoven, edge-reinforced filter membrane, drainage nonwoven and core, it being possible for additionally at least one further optionally edge-reinforced filter membrane to be arranged between the two drainage nonwovens. Here, the abovementioned components are all embedded in the at least one anchoring element.

In a further aspect, a method for producing the filter module is provided, the method comprising the following steps (a) to (h):
  (a) providing a membrane and a porous edge structure,
  (b) arranging the porous edge structure on at least one edge region on the membrane,
  (c) connecting the membrane to the porous edge structure arranged thereon,
  (d) optionally pleating the membrane having the porous edge structure arranged thereon,
  (e) optionally welding the membrane having the porous edge structure arranged thereon along the sides which do not have continuous edge reinforcement,
  (f) providing at least one anchoring element,
  (g) softening a subregion of the at least one anchoring element and
  (h) embedding the membrane having the porous edge structure arranged thereon in the softened subregion of the at least one anchoring element.

The above description regarding the filter module, including the membrane, the porous edge structure and the at least one anchoring element, apply analogously to the method for producing the filter module.

Steps (a) to (h) of the method for producing the filter module are explained more particularly below.

In step (a) of the method, a membrane and a porous edge structure are provided. In this regard, all the definitions and limitations as specified above in connection with the filter module in regard to the membrane and to the porous edge structure, especially with regard to the geometric shape, the pore size and the materials from which the membrane and the porous edge structure are constructed, apply to the method explained here. If, for instance, the membrane having the porous edge structure arranged thereon is to be welded in step (e), a membrane having a rectangular shape is suitably provided in step (a) of the method.

In step (b) of the method, the porous edge structure is arranged on at least one edge region on the membrane, i.e., at least one edge region of the membrane is covered by the porous edge structure, the porous edge structure preferably sitting flush with the membrane end. As mentioned in connection with the filter module, the porous edge structure can be arranged on multiple edge regions of the membrane, for example if embedding in two anchoring elements is to be carried out in step (h), as explained below.

In step (c) of the method, the membrane is connected to the porous edge structure arranged thereon, which may be achieved using heat and pressure treatment. For example, the membrane together with the porous edge structure arranged thereon is, to this end, guided into a heat sealer and heat-sealed, the sealing here being edge-sealing. Typically, the sealing process is done at an elevated pressure, with the membrane having the porous edge structure arranged thereon first passing through a heating press and then a cooling press. In the heating press, the membrane and the porous edge structure arranged on it are pressed together under pressure at an elevated temperature, thereby forming a firm composite, which is then cooled to ambient temperature in a cooling press, again under pressure. Advantageously, no adhesive at all is required for sealing, since the pores in the surface region of the membrane are filled in part with the softened material of the porous edge structure during the sealing operation, this contributing to the stability of the composite thus obtained. Typical process conditions of the sealing operation are a temperature of 120° C. to 300° C., a pressure of 1 to 5 bar and a speed of, for example, 23×30 mm/min without, however, being restricted thereto.

In a preferred embodiment of the method, the porous edge structure arranged on the membrane is provided with a texturing or a surface roughness during the connection operation in step (c). If the membrane is constructed from PTFE, which is a comparatively elastic material, and if the porous edge structure is constructed from PP, it is preferred that the membrane and the porous edge structure arranged on it are already surrounded by one or more support nonwovens, for example composed of polyphenylene sulfide (PPS), during heat-sealing. This leads, firstly, to an increased stability and, secondly, the nonwoven produces a texturing or surface roughness, since the texture of the nonwoven presses into the edge seal. If both the membrane and the porous edge structure are constructed from PES, heat-sealing can also be carried out without a nonwoven, since PES is more dimensionally stable owing to its lower elasticity. Nevertheless, to produce a texturing or surface roughness here, the membrane and the porous edge structure arranged on it can be guided over textured conveyor belts, for example over those composed of PTFE, during heat-sealing. In this case, the textured conveyor belts of the heat sealer serve not only to transport the membrane having the porous edge structure arranged thereon through the heat sealer, but also to produce a fiber impression. The textured conveyor belts, which are placed around the heating jaw of the heat sealer, in a way "press" into the material during heat-sealing and in this way produce the texturing or the surface roughness of the edge reinforcement. In principle, producing the texturing or the surface roughness is not restricted to the two embodiments described above. For instance, especially in the first-mentioned case (membrane: PTFE; porous edge structure: PP), texturing can also be achieved by the textured conveyor belts of the heat sealer, the heat-sealing taking place entirely without a nonwoven in this case. Depending on the nature of the membrane and the porous edge structure, a person skilled in the art will choose a suitable method for producing the texturing or the surface roughness in step (c), account also being taken here of the nature, especially the melting behavior, of optionally present nonwovens.

In step (d) of the method, the membrane having the porous edge structure arranged thereon that was previously processed to form a composite is optionally pleated. Suitable pleating methods are known to a person skilled in the art. Preferably, pleating is carried out at a temperature in the range from 50° C. to 200° C. As already mentioned in connection with the filter module, pleating is carried out such that both the membrane and the porous edge structure arranged on its edge region assume the fold structure caused by pleating. Optionally, a drainage nonwoven, if present, is concomitantly pleated in step (d).

In step (e) of the method, the membrane having the porous edge structure arranged thereon is optionally welded, the welding being done along the sides which do not have continuous edge reinforcement. As a result, the membrane having the porous edge structure arranged thereon assumes, for example, a tube shape, with one of the two edge regions or both edge regions on the tube exterior along the tube circumference being covered by the porous edge structure. Suitable welding methods, such as ultrasonic welding are known to a person skilled in the art.

In step (f) of the method, at least one anchoring element which serves to seal the membrane having the porous edge structure arranged thereon is provided. Also applicable in this context to the at least one anchoring element are all definitions and limitations as specified above in connection with the filter module, especially with regard to the geometric shape and the materials from which the at least one anchoring element is constructed. The geometric shape of the at least one anchoring element is, then, necessarily harmonized with the geometric shape of the membrane having the porous edge structure arranged thereon. By suitable selection of the materials, it is possible to deform the at least one anchoring element by input of heat, with the result that the membrane having the porous edge structure arranged thereon can be embedded therein. As already mentioned, the at least one anchoring element is particularly preferably constructed from polypropylene.

In addition to the at least one anchoring element, if necessary and in addition, a backflow safeguard, a core, at least one further filter membrane, which is optionally edge-reinforced, and a drainage nonwoven, typically in duplicate, may be provided—if this has not yet been done in step (c) or (d).

If the membrane having the porous edge structure arranged thereon assumes, for example, a tube shape, as optionally obtained by the welding in step (e), the embedding of the membrane having the porous edge structure arranged thereon in the at least one anchoring element is preceded by the backflow safeguard and the core being mounted around the tubular membrane or introduced into the tubular membrane. This also applies analogously to the drainage nonwoven and to an optionally present further filter membrane.

In step (g) of the method, a subregion of the at least one anchoring element is softened. This is done by a targeted input of heat at those sites where the membrane having the porous edge structure arranged thereon and also optionally present further components are to immerse for embedding. Suitable devices which allow a targeted input of heat are described in the prior art, the input of heat being adapted as a routine practice by a person skilled in the art to the material from which the at least one anchoring element is constructed.

In step (h) of the method, the membrane having the porous edge structure arranged thereon together with optionally present further components is embedded in the softened subregion of the at least one anchoring element. Here, the porous edge structure and the correspondingly covered edge region of the membrane need not necessarily completely immerse into the respective anchoring element. If the porous edge structure is not arranged just on a single edge region of the membrane, embedding can be carried out in more than one anchoring element in step (h). If the membrane is, for example, a tubular membrane, as optionally obtained by the welding in step (e), the two edge regions of the membrane having the porous edge structure arranged thereon can be embedded in corresponding anchoring elements. After embedding the membrane having the porous edge structure arranged thereon in the at least one anchoring element, the filter module thus obtained is lastly additionally cooled to ambient temperature.

Before actual use, the filter module produced using the method is installed in a housing made of metal or plastic ("filter capsule"), resulting in a filter module having a defined input and output. If necessary, the filter module thus installed can finally additionally be sterilized with γ-radiation. Typical radiation doses are in the range from 10 to 200 kGy. Alternatively, it is also possible to carry out autoclaving or inline steaming at 120° C. to 140° C. for 20 to 30 min. This ensures that the filter module is free of pathogens, which is required for a multiplicity of applications.

Owing to the edge reinforcement of the membrane with the porous edge structure, the described embedding in the at least one anchoring element provides a fluid-tight connection of the above components. In other words, the occurrence of leaks in the edge region can be completely prevented thereby, the result being that the filter module has a sufficient sterility even over a relatively long period of use. As a result, the filter module is particularly suitable for sterile-filtration and virus filtration of fluid media, particularly of gaseous media, especially of air, as well as of liquid media.

In another aspect, the use of the filter module for sterile-filtration or virus filtration of a fluid medium is provided, the fluid medium preferably being a gaseous medium, particularly preferably air, or a liquid medium.

DETAILED DESCRIPTION

EXAMPLES

The following examples serve to further explain and illustrate the present invention without, however, being restricted thereto.

Example A

The influence of edge reinforcement on filter sterility was evaluated on the basis of bacterial retention. To this end, a filter module having an edge-reinforced membrane and a filter module without an edge-reinforced membrane as a comparative example were tested. In both cases the membrane was constructed from expanded polytetrafluoroethylene. The edge reinforcement of the filter module, which edge reinforcement was sealed on the inflow side, was constructed from polypropylene, as were the end caps used in both cases. Drainage nonwovens composed of polyphenylene sulfide were used for stabilization in both cases.

Figure 1:
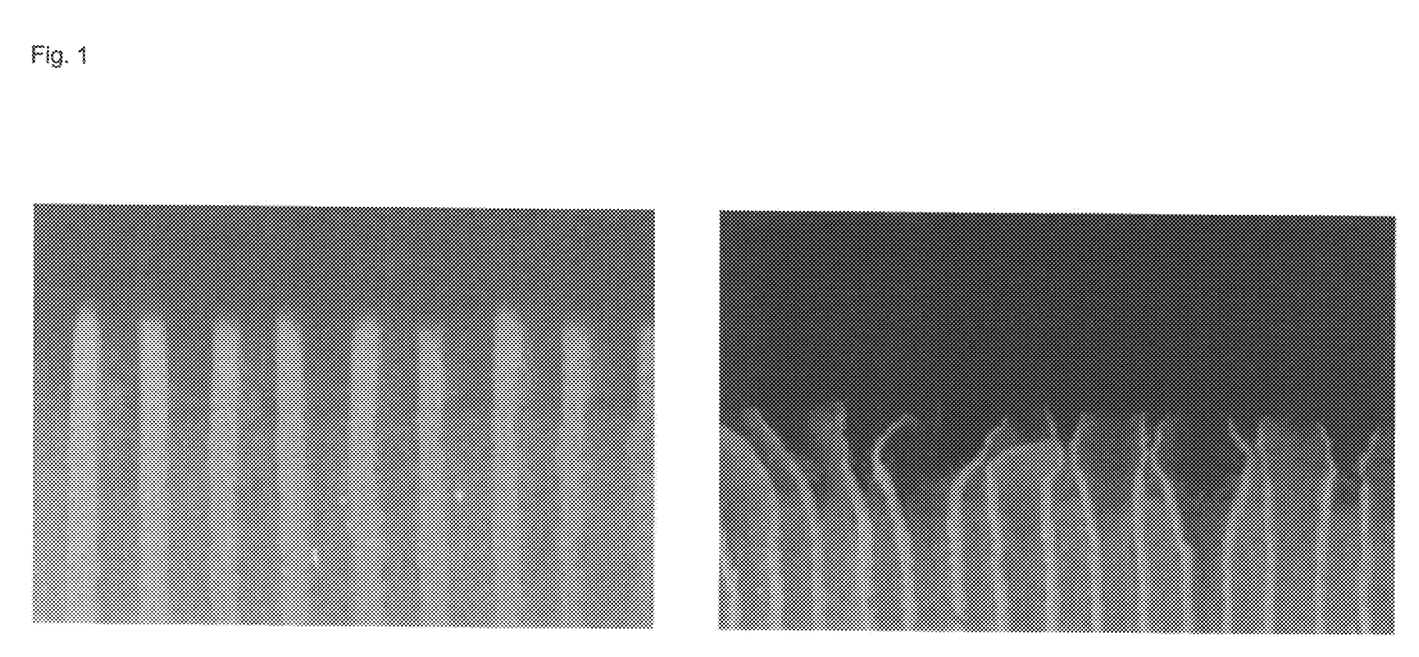
FIG. 1 shows scanning electron microscopy images of a filter module having an edge-reinforced membrane according to the present invention (left) and of a filter module without an edge-reinforced membrane as a comparative example (right). In both cases, the membranes are pleated. As can be gathered from FIG. 1, the edge region of the membrane is uniformly interlocked with the anchoring element in the case of the presence of the edge reinforcement, whereas the edge region of the membrane tends to bend down or bend over in the case of the absence of the edge reinforcement. This becomes apparent especially in the folds of the pleating, which, in a sense, fall over.

Table A-1 shows the sterility results from a BC ("Bacteria Challenge") test for the filter module without an edge-reinforced membrane (Example No. 1 to 10). The BC test was carried out in accordance with ASTM 838-05. The filter module without an edge-reinforced membrane was consistently 10-inch filter cartridges, the ePTFE membrane (length: 241 mm; thickness: 90±10 μm) having a pore size of 0.2 μm. Altogether, five cartridges, each from two different lots, were tested. As can be gathered from Table A-1, the filter module without edge reinforcement already shows a comparatively high microbial count in the untreated state, i.e., nonsteamed state due to the insufficient connection of the membrane to the end cap (see also the SEM image in FIG. 1, right), which ultimately leads to a lack of sterility of the filter module.

Figure 2:
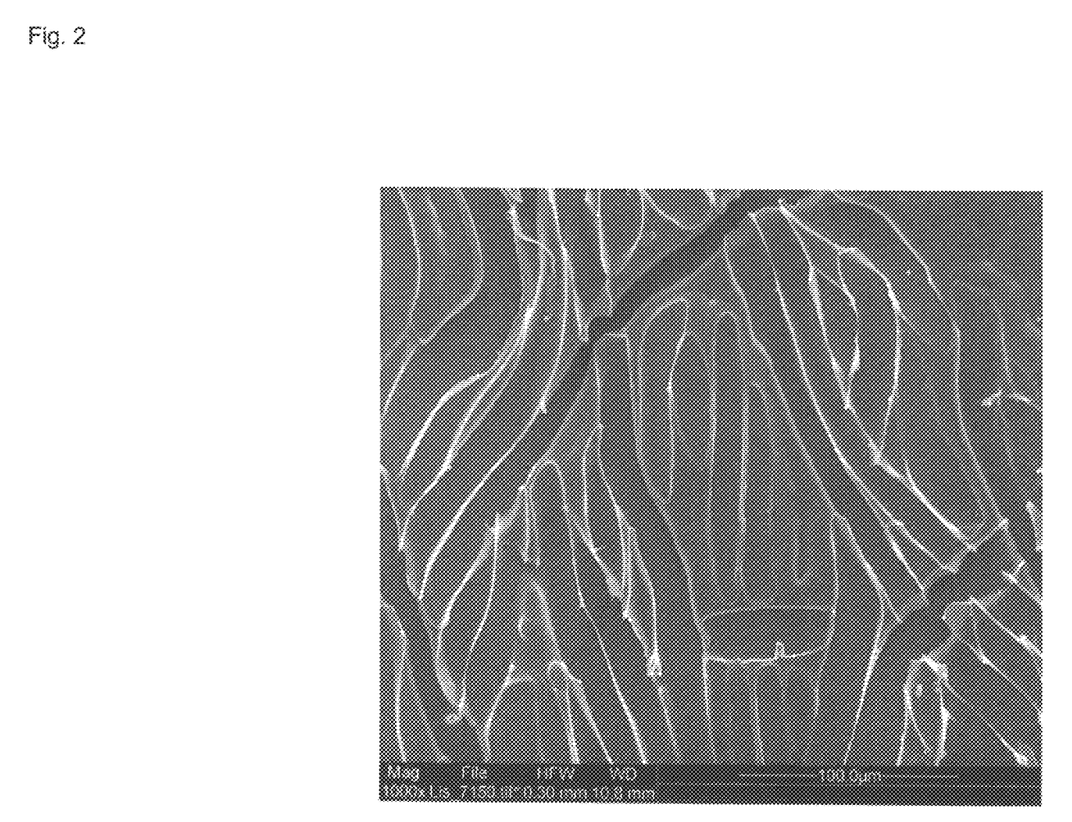
FIG. 2 shows the texturing or the surface roughness when looking from above at the example of a filter module according to the invention having a PTFE membrane and a PP edge strip arranged thereon. As can be gathered from FIG. 2, the texture of the nonwoven has pressed into the edge strip. On the basis of the SEM image from FIG. 2, it is possible to determine the gap width of the texturing or the surface roughness.
Figure 3:
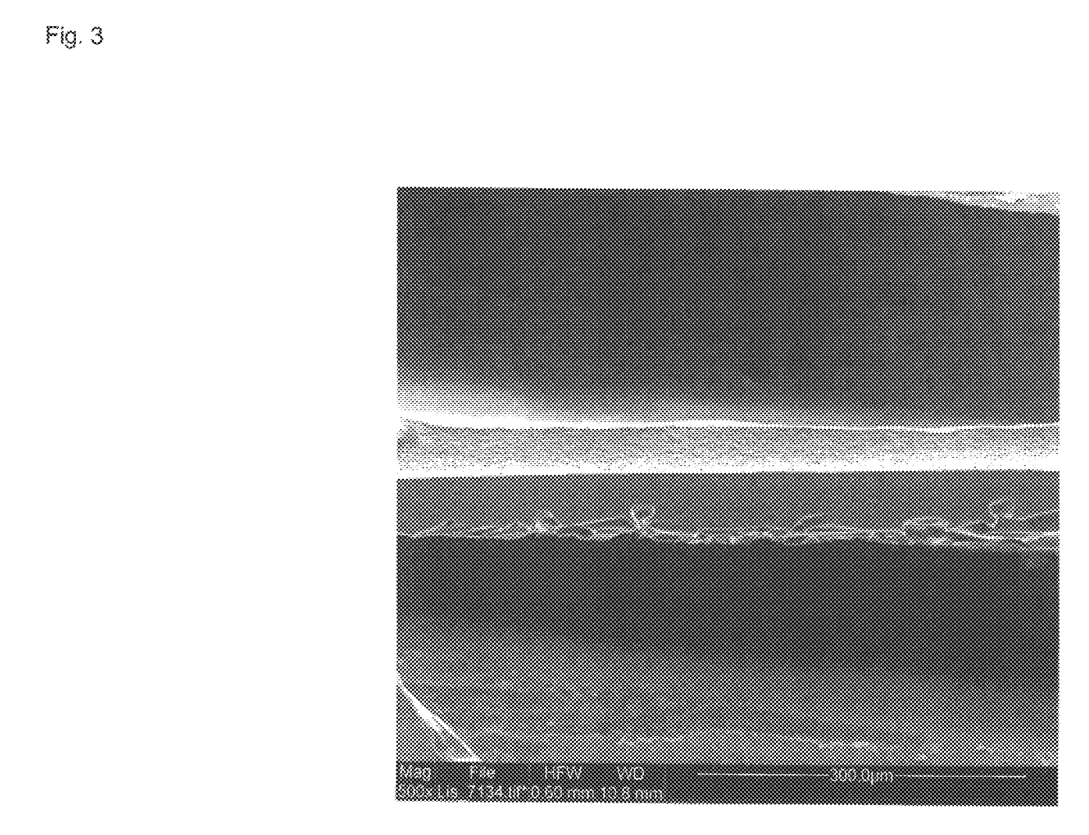
FIG. 3 shows the nonwoven-attributed texturing or surface roughness of the filter module according to the invention from FIG. 2 when looking from the side. On the basis of the SEM image from FIG. 3, it is possible to determine the penetration depth of the texturing or of the surface roughness.

Tables A-2 to A-4 show the sterility results for the filter module having an edge-reinforced membrane (Example No. 11 to 36). Here, the BC test was also carried out in accordance with ASTM 838-05. The filter module having an edge-reinforced membrane was, too, consistently 10-inch filter cartridges, the ePTFE membrane (length: 241 mm; thickness: 90±10 μm) having a pore size of 0.2 μm. The porous edge structure used was a PP membrane (thickness: 180±20 μm) in strip form having a pore size of likewise 0.2 μm and an edge region/width of 8 mm, i.e., about 3.3% of the total area of the filter membrane were covered by such a porous edge structure. Heat-sealing was carried out at a temperature of 170° C. and at a pressure of 3 bar. The PPS drainage nonwoven was already concomitantly guided during the sealing operation. As a result of the fiber impression by the nonwoven, a texturing or a surface roughness was produced in the porous edge structure. The average gap width was 16 μm, whereas the average penetration depth was 11 μm, which could be ascertained by scanning electron microscopy (see also the SEM images in FIG. 2 and in FIG. 3). The penetration depth of the edge seal into the end cap was about 1.5 to 2 mm, i.e., a protrusion/overhang of 6 to 6.5 mm protruding from the end cap. Ten cartridges from one lot and also four or twelve cartridges from two further lots were tested. As can be gathered from Tables A-2 to A-4, no significant microbial count is measurable even in the case of an up to 150 times steaming of the filter module having edge reinforcement (134° C. and 30 min for each cycle, followed by cooling with water to about 15° C.). The reason therefor is the improved connection of the edge-reinforced membrane to the end cap (see also the SEM image in FIG. 1, left), the result being that especially leaks in the edge region can be avoided, which leaks would otherwise have an adverse effect on the sterility of the filter module.

Example B

In a further system, the influence of edge reinforcement on filter sterility was evaluated on the basis of bacteriophage retention. To this end, a filter module having an edge-reinforced membrane and a filter module without an edge-reinforced membrane as a comparative example were tested. Here too, 10-inch filter cartridges were consistently used. In both cases, the membrane was constructed from polyethersulfone and had hydrophilic properties due to the addition of polyvinylpyrrolidone, and two plies each of an identical virus membrane were installed as prefilter and main filter. The pore size of the filter membranes was 0.02 μm. Whereas the prefilter was edge-reinforced in the example, the prefilter in the comparative example did not have edge reinforcement. The edge reinforcement, i.e., the porous edge structure, of the filter module, which edge reinforcement was sealed on the prefilter on the inflow side, was likewise constructed from polyethersulfone and had a pore size of 0.65 μm. The thickness of the prefilter membrane and main-filter membrane was 150±10 μm in each case, whereas the thickness of the edge strip was 160±20 μm. Heat-sealing was carried out at a temperature of 270° C. and at a pressure of 4 bar. The texturing or surface roughness was produced by impression of the textured PTFE conveyor belt of the heat sealer. The fiber thickness of the textured conveyor belt was in the region of 400 μm, which could be measured on the basis of microscopy images. Moreover, a penetration depth of about 15 to 20 μm was obtained. The edge region/width and the penetration depth into the end cap were identical to the values from Example A. The end caps were constructed from polypropylene, both in the example according to the invention and in the comparative example. Moreover, PP drainage nonwovens were used in both cases.

Table B shows the sterility results for the filter module without an edge-reinforced membrane (Example No. I) and for the filter module having an edge-reinforced membrane (Example No. II to IV). In the case of the filter module without edge reinforcement, an LRV ("Log 10 Reduction Value") of 4.3 was ascertained. In contrast to a complete retention, this value merely corresponds to a reduction in the original bacteriophage concentration, i.e., it was additionally possible to detect bacteriophages in the filtrate. By contrast, in the case of the edge-reinforced filter module, an LRV of 6.0 was ascertained, this amounting to a complete retention of bacteriophages. In comparison with the filter module without an edge-reinforced membrane, this is an improvement of about two log levels.

Here, the testing of bacteriophage retention was carried out on the basis of a phage solution composed of Pseudomonas aeruginosa bacteriophages PP7 having a concentration of at least $10^7$ PFU/mL, which was filtered at a constant pressure of 2 bar through the filter module to be tested. For the filtration, the fractions were not collected in various containers, but all collected together in one pool. The filtrate thus obtained was subsequently tested for phages.

To analyze the bacteriophage PP7 titer, samples (150 μL aliquot) were incubated with bacteria (150 μL aliquot of an overnight culture, diluted 1:100 in nutrient solution) at room temperature for about 10 minutes. Thereafter, 2.5 mL of 0.8% agar were added and the entire volume was spread on a Petri dish containing 1.5% solid nutrient agar. After an incubation time of 18 to 24 hours at 37° C., the plaques induced by the bacteriophages were counted.

TABLE A-1

| Example No. | Cartridge No. | Lot No. | Treatment method | Test microbe | Applied microbial count | Microbial load [microbes/cm$^2$] | Microbial count [CFU] |
|---|---|---|---|---|---|---|---|
| 1 | 1 | 1 | Untreated | Brevundimonas dim | $8.00 \times 10^{10}$ | $1.43 \times 10^7$ | 0 |
| 2 | 2 | 1 | Untreated | Brevundimonas dim | $8.00 \times 10^{10}$ | $1.43 \times 10^7$ | 352 |
| 3 | 3 | 1 | Untreated | Brevundimonas dim | $8.00 \times 10^{10}$ | $1.43 \times 10^7$ | 0 |
| 4 | 4 | 1 | Untreated | Brevundimonas dim | $8.00 \times 10^{10}$ | $1.43 \times 10^7$ | 40 |
| 5 | 5 | 1 | Untreated | Brevundimonas dim | $8.00 \times 10^{10}$ | $1.43 \times 10^7$ | 0 |
| 6 | 1 | 2 | Untreated | Brevundimonas dim | $8.00 \times 10^{10}$ | $1.43 \times 10^7$ | 0 |
| 7 | 2 | 2 | Untreated | Brevundimonas dim | $8.00 \times 10^{10}$ | $1.43 \times 10^7$ | No longer countable |
| 8 | 3 | 2 | Untreated | Brevundimonas dim | $8.00 \times 10^{10}$ | $1.43 \times 10^7$ | 400 |
| 9 | 4 | 2 | Untreated | Brevundimonas dim | $8.00 \times 10^{10}$ | $1.43 \times 10^7$ | 338 |
| 10 | 5 | 2 | Untreated | Brevundimonas dim | $8.00 \times 10^{10}$ | $1.43 \times 10^7$ | 52 |

| Example No. | Cartridge No. | Lot No. | Membrane area [m$^2$] | Bubble point [bar] | | Test pressure [bar] | Diffusion [mL/min] | |
|---|---|---|---|---|---|---|---|---|
| | | | | before sterilization | after BC test | | before sterilization | after BC test |
| 1 | 1 | 1 | 0.56 | 1.64 | 1.60 | 0.70 | 2.2 | 1.5 |
| 2 | 2 | 1 | 0.56 | 1.59 | 1.55 | 0.70 | 2.1 | 1.6 |
| 3 | 3 | 1 | 0.56 | 1.69 | 1.64 | 0.70 | 2.2 | 1.5 |
| 4 | 4 | 1 | 0.56 | 1.65 | 1.63 | 0.70 | 2.4 | 1.5 |
| 5 | 5 | 1 | 0.56 | 1.60 | 1.54 | 0.70 | 2.3 | 1.8 |
| 6 | 1 | 2 | 0.56 | 1.60 | 1.55 | 0.70 | 11.0 | 1.7 |
| 7 | 2 | 2 | 0.56 | 1.60 | 1.55 | 0.70 | 11.5 | 2.8 |
| 8 | 3 | 2 | 0.56 | 1.60 | 1.59 | 0.70 | 11.1 | 2.1 |
| 9 | 4 | 2 | 0.56 | 1.64 | 1.63 | 0.70 | 9.9 | 1.6 |
| 10 | 5 | 2 | 0.56 | 1.64 | 1.63 | 0.70 | 10.7 | 1.7 |

TABLE A-2

| Example No. | Cartridge No. | Lot No. | Treatment method | Test microbe | Applied microbial count | Microbial load [microbes/cm$^2$] | Microbial count [CFU] |
|---|---|---|---|---|---|---|---|
| 11 | 1 | 1 | Untreated | Brevundimonas dim | $8.75 \times 10^{10}$ | $1.46 \times 10^7$ | 0 |
| 12 | 2 | 1 | 150x steamed | Brevundimonas dim | $7.50 \times 10^{10}$ | $1.25 \times 10^7$ | 0 |
| 13 | 3 | 1 | Untreated | Brevundimonas dim | $8.75 \times 10^{10}$ | $1.46 \times 10^7$ | 0 |
| 14 | 4 | 1 | 150x steamed | Brevundimonas dim | $7.50 \times 10^{10}$ | $1.25 \times 10^7$ | 0 |
| 15 | 5 | 1 | 150x steamed | Brevundimonas dim | $7.50 \times 10^{10}$ | $1.25 \times 10^7$ | 0 |
| 16 | 6 | 1 | 150x steamed | Brevundimonas dim | $7.50 \times 10^{10}$ | $1.25 \times 10^7$ | 0 |
| 17 | 7 | 1 | Untreated | Brevundimonas dim | $8.75 \times 10^{10}$ | $1.46 \times 10^7$ | 0 |
| 18 | 8 | 1 | 150x steamed | Brevundimonas dim | $7.50 \times 10^{10}$ | $1.25 \times 10^7$ | 0 |
| 19 | 9 | 1 | Untreated | Brevundimonas dim | $8.75 \times 10^{10}$ | $1.46 \times 10^7$ | 0 |
| 20 | 10 | 1 | Untreated | Brevundimonas dim | $8.75 \times 10^{10}$ | $1.46 \times 10^7$ | 0 |

| Example No. | Cartridge No. | Lot No. | Membrane area [m$^2$] | Bubble point [bar] before sterilization | Bubble point [bar] after BC test | Test pressure [bar] | Diffusion [mL/min] before sterilization | Diffusion [mL/min] after BC test |
|---|---|---|---|---|---|---|---|---|
| 11 | 1 | 1 | 0.60 | — | — | 0.70 | — | 2.6 |
| 12 | 2 | 1 | 0.60 | — | 1.59 | 0.70 | — | 2.9 |
| 13 | 3 | 1 | 0.60 | — | — | 0.70 | — | 2.9 |
| 14 | 4 | 1 | 0.60 | — | 1.58 | 0.70 | — | 2.1 |
| 15 | 5 | 1 | 0.60 | — | 1.60 | 0.70 | — | 1.4 |
| 16 | 6 | 1 | 0.60 | — | 1.59 | 0.70 | — | 5.4 |
| 17 | 7 | 1 | 0.60 | — | — | 0.70 | — | 3.3 |
| 18 | 8 | 1 | 0.60 | — | 1.54 | 0.70 | — | 2.9 |
| 19 | 9 | 1 | 0.60 | — | — | 0.70 | — | 2.8 |
| 20 | 10 | 1 | 0.60 | — | — | 0.70 | — | 2.6 |

TABLE A-3

| Example No. | Cartridge No. | Lot No. | Treatment method | Test microbe | Applied microbial count | Microbial load [microbes/cm$^2$] | Microbial count [CFU] |
|---|---|---|---|---|---|---|---|
| 21 | 1 | 2 | 25x steamed | Brevundimonas dim | $8.00 \times 10^{10}$ | $1.33 \times 10^7$ | 0 |
| 22 | 2 | 2 | Untreated | Brevundimonas dim | $7.75 \times 10^{10}$ | $1.29 \times 10^7$ | 0 |
| 23 | 3 | 2 | Untreated | Brevundimonas dim | $7.75 \times 10^{10}$ | $1.29 \times 10^7$ | 0 |
| 24 | 4 | 2 | 25x steamed | Brevundimonas dim | $8.00 \times 10^{10}$ | $1.33 \times 10^7$ | 0 |
| 25 | 1 | 3 | Untreated | Brevundimonas dim | $7.25 \times 10^{10}$ | $1.32 \times 10^7$ | 0 |
| 26 | 2 | 3 | Untreated | Brevundimonas dim | $7.25 \times 10^{10}$ | $1.32 \times 10^7$ | 0 |
| 27 | 3 | 3 | Untreated | Brevundimonas dim | $7.25 \times 10^{10}$ | $1.32 \times 10^7$ | 0 |
| 28 | 4 | 3 | Untreated | Brevundimonas dim | $7.25 \times 10^{10}$ | $1.32 \times 10^7$ | 0 |
| 29 | 5 | 3 | Untreated | Brevundimonas dim | $7.25 \times 10^{10}$ | $1.32 \times 10^7$ | 0 |
| 30 | 6 | 3 | Untreated | Brevundimonas dim | $7.25 \times 10^{10}$ | $1.32 \times 10^7$ | 0 |

| Example No. | Cartridge No. | Lot No. | Membrane area [m$^2$] | Bubble point [bar] before sterilization | Bubble point [bar] after BC test | Test pressure [bar] | Diffusion [mL/min] before sterilization | Diffusion [mL/min] after BC test |
|---|---|---|---|---|---|---|---|---|
| 21 | 1 | 2 | 0.60 | — | 1.59 | 0.70 | — | 3.8 |
| 22 | 2 | 2 | 0.60 | — | 1.65 | 0.70 | — | 3.5 |
| 23 | 3 | 2 | 0.60 | — | 1.65 | 0.70 | — | 2.1 |
| 24 | 4 | 2 | 0.60 | — | 1.59 | 0.70 | — | 3.0 |
| 25 | 1 | 3 | 0.55 | — | 1.55 | 0.70 | — | 1.0 |
| 26 | 2 | 3 | 0.55 | — | 1.54 | 0.70 | — | 2.0 |
| 27 | 3 | 3 | 0.55 | — | 1.49 | 0.70 | — | 1.7 |
| 28 | 4 | 3 | 0.55 | — | 1.55 | 0.70 | — | 2.6 |
| 29 | 5 | 3 | 0.55 | — | 1.53 | 0.70 | — | 1.9 |
| 30 | 6 | 3 | 0.55 | — | 1.50 | 0.70 | — | 1.9 |

TABLE A-4

| Example No. | Cartridge No. | Lot No. | Treatment method | Test microbe | Applied microbial count | Microbial load [microbes/$cm^2$] | Microbial count [CFU] |
|---|---|---|---|---|---|---|---|
| 31 | 7 | 3 | Untreated | Brevundimonas dim | $8.50 \times 10^{10}$ | $1.55 \times 10^7$ | 0 |
| 32 | 8 | 3 | Untreated | Brevundimonas dim | $8.50 \times 10^{10}$ | $1.55 \times 10^7$ | 0 |
| 33 | 9 | 3 | Untreated | Brevundimonas dim | $8.50 \times 10^{10}$ | $1.55 \times 10^7$ | 0 |
| 34 | 10 | 3 | Untreated | Brevundimonas dim | $8.50 \times 10^{10}$ | $1.55 \times 10^7$ | 0 |
| 35 | 11 | 3 | Untreated | Brevundimonas dim | $8.50 \times 10^{10}$ | $1.55 \times 10^7$ | 0 |
| 36 | 12 | 3 | Untreated | Brevundimonas dim | $8.50 \times 10^{10}$ | $1.55 \times 10^7$ | 0 |

| Example No. | Cartridge No. | Lot No. | Membrane area [$m^2$] | Bubble point [bar] before sterilization | Bubble point [bar] after BC test | Test pressure [bar] | Diffusion [mL/min] before sterilization | Diffusion [mL/min] after BC test |
|---|---|---|---|---|---|---|---|---|
| 31 | 7 | 3 | 0.55 | — | 1.54 | 0.70 | — | 2.2 |
| 32 | 8 | 3 | 0.55 | — | 1.50 | 0.70 | — | 1.8 |
| 33 | 9 | 3 | 0.55 | — | 1.55 | 0.70 | — | 2.2 |
| 34 | 10 | 3 | 0.55 | — | 1.50 | 0.70 | — | 4.3 |
| 35 | 11 | 3 | 0.55 | — | 1.54 | 0.70 | — | 2.2 |
| 36 | 12 | 3 | 0.55 | — | 1.55 | 0.70 | — | 1.7 |

TABLE B

| Example No. | Lot No. | Filter area [$cm^2$] | Prefilter | Main filter | Prediffusion [mL/min] | Postdiffusion [mL/min] |
|---|---|---|---|---|---|---|
| I | 1 | 6500 | Not sealed | Not sealed | 11.0 | 9.5 |
| II | 1 | 5189 | Sealed | Not sealed | 11.0 | 11.4 |
| III | 2 | 5497 | Sealed | Not sealed | 10.6 | 11.4 |
| IV | 2 | 5497 | Sealed | Not sealed | 9.6 | 10.9 |

| Example No. | Lot No. | Fractions [mL] | Titer, L2 PFU/mL | Titer, fractions PFU/mL | Plaques? | LRV |
|---|---|---|---|---|---|---|
| I | 1 | Pool | $1.8 \times 10^7$ | $8.5 \times 10^2$ | Bacteriophages in the filtrate | 4.3 |
| II | 1 | Pool | $1.8 \times 10^7$ | $2.0 \times 10^1$ (*) | Complete retention | 6.0 |
| III | 2 | Pool | $1.8 \times 10^7$ | $2.0 \times 10^1$ (*) | Complete retention | 6.0 |
| IV | 2 | Pool | $1.8 \times 10^7$ | $2.0 \times 10^1$ (*) | Complete retention | 6.0 |

(*) No phages were detected in the filtrate. The specified values are calculated statistical values in order to be able to estimate the detection limit (see also "Guidance for industry—Q5A viral safetyevaluation of biotechnology products derived from cell lines of human or animal origin").

A filter module based on an edge-reinforced membrane is provided. The edge reinforcement achieves a fluid-tight connection of the filter membrane to the anchoring element. In particular, the production method can virtually completely prevent the occurrence of leaks in the edge region of the filter module, which leaks would otherwise have an adverse effect on the sterility of the filter module. Advantageously, this can ensure an adequate sterility even over a relatively long period of use, and this means that the filter module is suitable for all those applications that require an absence of bacteria and viruses. The filter module is thus outstandingly suitable for the sterile-filtration and virus filtration of fluid media, particularly of gaseous media, especially of air, as well as of liquid media.

What is claimed is:

1. A filter module comprising:
   a filter membrane having an edge region;
   a porous edge structure connected to the edge region of the filter membrane; and
   at least one anchoring element,
   wherein at least part of the filter membrane and at least part of the porous edge structure connected thereto are embedded together in the at least one anchoring element,
   wherein the porous edge structure is formed as an edge strip which covers the edge region without completely covering a remainder of the filter membrane and reinforces the edge region when embedded with the filter membrane in the at least one anchoring element, and
   wherein the edge strip sits flush with an end of the filter membrane when embedded in the at least one anchoring element to stabilize the edge region of the filter membrane by reducing a risk of the membrane edge region bending, buckling or breaking off.

2. The filter module as claimed in claim 1, wherein the filter membrane and the porous edge structure connected to the edge region are present as a composite.

3. The filter module as claimed in claim 1, wherein the porous edge structure has a pore size of at least 0.1 µm.

4. The filter module as claimed in claim 1, wherein the porous edge structure is textured or has a surface roughness.

5. The filter module as claimed in claim 1, wherein part of the porous edge structure remains outside the at least one anchoring element and forms a protrusion or overhang.

6. The filter module as claimed in claim 1, wherein the filter membrane is tubular.

7. The filter module as claimed in claim 1, wherein the filter membrane is pleated.

8. The filter module as claimed in claim 1, wherein the filter membrane is constructed from a polymer selected from the group consisting of polytetrafluoroethylene, polyvinylidene fluoride, polyethersulfone, polyamide, polyolefin, cellulose acetate, cellulose, and mixtures thereof.

9. The filter module as claimed in claim 1, wherein the porous edge structure is constructed from a polymer selected from the group consisting of polyethersulfone, polyamide, polyolefin, and mixtures thereof.

10. The filter module as claimed in claim 1, wherein the filter membrane is constructed from polytetrafluoroethylene, and wherein both the porous edge structure and the at least one anchoring element are constructed from polypropylene.

11. The filter module as claimed in claim 1, wherein:
the filter membrane and the porous edge structure are constructed from polyethersulfone, and
the at least one anchoring element is constructed from polypropylene.

12. The filter module as claimed in claim 1, wherein the porous edge structure is a porous film or a membrane.

13. A method for producing the filter module as claimed in claim 1, comprising the following steps:
(a) providing a filter membrane and a porous edge structure,
(b) arranging the porous edge structure on at least one edge region on the filter membrane,
(c) connecting the filter membrane to the porous edge structure arranged on the at least one edge region,
(d) optionally pleating the filter membrane having the porous edge structure arranged on the at least one edge region,
(e) optionally welding the filter membrane having the porous edge structure arranged on the at least one edge region along sides of the filter membrane which do not have continuous edge reinforcement,
(f) providing at least one anchoring element,
(g) softening a subregion of the at least one anchoring element, and
(h) embedding the filter membrane having the porous edge structure arranged on the at least one edge region in the softened subregion of the at least one anchoring element.

14. The method as claimed in claim 13, wherein the porous edge structure is textured or is provided with a surface roughness during the connection operation in step (c).

15. A method of filtering a fluid medium, comprising passing the fluid medium through a filter module according to claim 1.

16. The method according to claim 15, wherein the fluid medium is air.

17. The method according to claim 13, comprising pleating the filter membrane having the porous edge structure arranged on the at least one edge region.

18. The method according to claim 13, comprising welding the filter membrane along the sides which do not have continuous edge reinforcement.

19. The method according to claim 17, comprising welding the filter membrane along the sides which do not have continuous edge reinforcement.

20. The filter module as claimed in claim 5, wherein the protrusion or overhang extends outside from an embedding side of the at least one anchoring element at least 1 to 10 mm.

21. The filter module as claimed in claim 1, wherein:
the filter membrane has a total area,
the edge strip has a width of approximately 2 to 10 mm, and
the edge region of the filter membrane covered by the edge strip accounts for about 0.5% to 25% of the total area of the filter membrane.

* * * * *